United States Patent [19]

Mar et al.

[11] Patent Number: 5,542,173
[45] Date of Patent: Aug. 6, 1996

[54] METHOD OF MAKING FLEXIBLE DEFIBRILLATION ELECTRODE

[75] Inventors: Craig E. Mar, Fremont; Benjamin D. Pless, Menlo Park; M. Elizabeth Bush, Fremont, all of Calif.

[73] Assignee: Ventritex, Inc., Sunnyvale, Calif.

[21] Appl. No.: 388,766

[22] Filed: Feb. 15, 1995

Related U.S. Application Data

[62] Division of Ser. No. 126,619, Sep. 24, 1993, Pat. No. 5,439,485.

[51] Int. Cl.⁶ .................................................. H01R 43/00
[52] U.S. Cl. ............................ 29/825; 156/143; 607/119; 607/122
[58] Field of Search ................................ 29/825; 174/47; 156/143, 196; 264/209.1

[56] References Cited

U.S. PATENT DOCUMENTS

| | | | |
|---|---|---|---|
| 3,572,344 | 3/1971 | Bolduc | 128/418 |
| 3,788,329 | 1/1974 | Friedman | 128/419 |
| 4,161,952 | 7/1979 | Kinney et al. | 128/786 |
| 4,698,890 | 10/1987 | Neaves . | |
| 4,860,769 | 8/1989 | Fogarty et al. | 128/786 |
| 4,904,431 | 2/1990 | O'Maleki | 156/143 X |
| 4,922,927 | 5/1990 | Fine et al. | 128/786 |
| 4,998,975 | 3/1991 | Cohen et al. | 128/419 |
| 5,007,422 | 4/1991 | Pless et al. | 28/419 |
| 5,007,436 | 4/1991 | Smits | 128/786 |
| 5,016,808 | 5/1991 | Heil, Jr. et al. | 228/176 |
| 5,052,407 | 10/1991 | Hauser et al. | 128/786 |
| 5,115,818 | 5/1992 | Holleman et al. | 128/784 |
| 5,144,960 | 9/1992 | Mehra et al. | 128/786 |
| 5,171,262 | 12/1992 | MacGregor . | |
| 5,174,288 | 12/1992 | Bardy et al. | 128/419 |
| 5,226,260 | 7/1993 | Mar et al. | 51/319 |
| 5,265,623 | 11/1993 | Kroll et al. | 607/122 |

FOREIGN PATENT DOCUMENTS

| | | |
|---|---|---|
| 251265 | 1/1988 | European Pat. Off. . |
| 473045 | 3/1992 | European Pat. Off. . |
| 9213481 | 8/1992 | WIPO . |

OTHER PUBLICATIONS

"A subcutaneoous Lead Array for Implantable Cardioverter Defibrillators", Luc Jordaens, et al., PACE, vol. 16, Jul. 1993, Part I, pp. 1429–1433.

*Primary Examiner*—Carl J. Arbes
*Attorney, Agent, or Firm*—Steven M. Mitchell; M. Elizabeth Bush; Mark J. Meltzer

[57] ABSTRACT

An implantable defibrillator lead comprises a flexible core onto which is wound helically wound coils to form an electrode. These electrode coils are partially encapsulated by a flexible matrix which holds them in their wrapped position around the core. Due to its coiled coil structure, this electrode provides improved flexibility, and can be used endocardially, intravascularly, epicardially, or subcutaneously. The electrode may function alternately as a defibrillation electrode and as a sensing electrode in a lead with a separate pacing electrode.

22 Claims, 10 Drawing Sheets

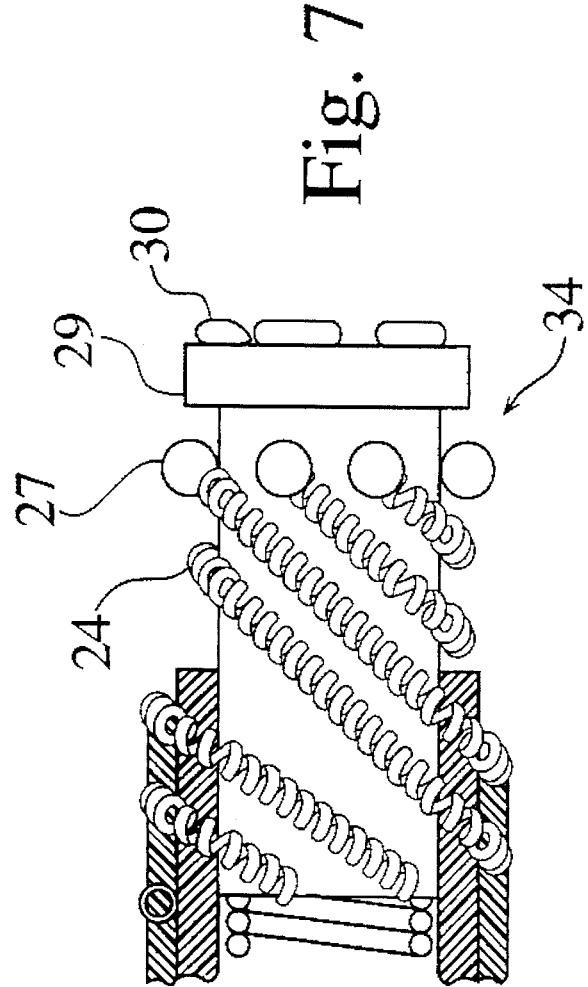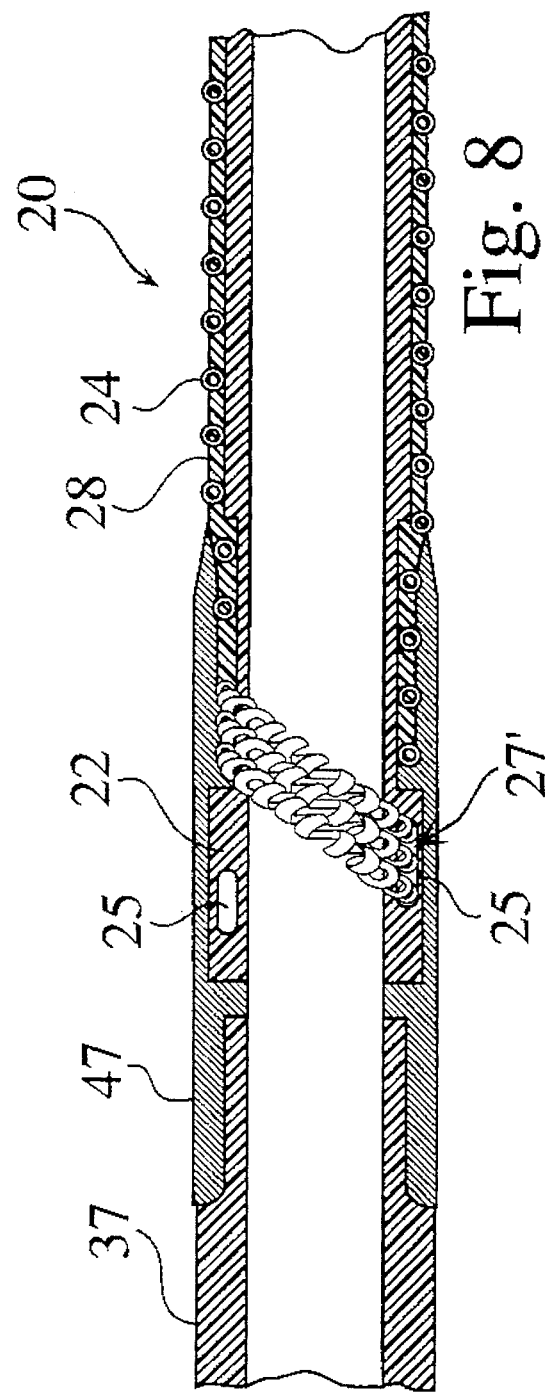

METHOD OF MAKING FLEXIBLE DEFIBRILLATION ELECTRODE

This is a divisional of application Ser. No. 08/126,619, filed on Sep. 24, 1993, now U.S. Pat. No. 5,439,485 issued Apr. 8, 1995.

FIELD OF THE INVENTION

This invention relates to medical electrical stimulation electrodes in general and to implantable defibrillation electrodes in particular.

BACKGROUND OF THE INVENTION

It is well known that cardiac arrhythmias such as ventricular fibrillation may be controlled with devices such as implantable defibrillators. Many different types of defibrillation electrodes have been suggested over the years, as can be seen from the following examples. In this discussion, no distinction will be made between cardioversion and defibrillation; both will be referred to as defibrillation.

U.S. Pat. No. 3,942,536 issued to Mirowski et al. discloses an intravascular bipolar catheter electrode system wherein each of two electrodes is composed of a plurality of spaced, low impedance rings. As implanted, the first electrode is located within the right ventricle (RV) and the second electrode is located in the superior vena cava (SVC).

In U.S. Pat. No. 4,161,952 issued to Kinney et al., a catheter electrode has a coil of wound spring wire, with filler material beneath and between individual turns of coil such that only the outside of the wound wire is exposed to the patient's body. It is designed to reside in or about the heart, as in the SVC or in the coronary sinus (CS).

U.S. Pat. No. 4,922,927 issued to Fine et al. teaches the use of tightly wound wire forming a tight coil on a support that is flared to provide a greater diameter along its midsection than at its ends, to form an RV electrode. A copper-zirconium alloy wrapped with tantalum and coated with iridium oxide is suggested for the tightly wound wire.

Other types of transvenously placed leads are disclosed in U.S. Pat. No. 4,998,975 issued to Cohen et al. One lead is placed through the heart wall, and into the pericardial space, and another is placed endocardially in a conventional manner. Both leads are shown with several embodiments, with the examples of general electrode construction being to expose a section of the conductor coil, or to use ring electrodes similar to those used in conventional bipolar pacemaker leads. Cohen et al. also describe two methods for steering more current to a selected region of the heart. The first method is to apply various voltages to the connectors of each of four electrodes. The second method uses the resistance of conductors, both between connector and electrode, and between two electrodes on the same lead, and the body tissue resistance between electrodes on different leads, to form a voltage divider, thus creating a different potential at each electrode.

Another lead system patent, U.S. Pat. No. 5,007,436 issued to Smits, describes electrodes of both J and straight configurations, for use in the RV, right atrium, great cardiac vein, or CS. The fabrication methods suggested use close wound conductive coils mounted exterior to an elongated insulative sheath, or the method of Kinney et al.

Spiral shaped electrodes for endocardial, epicardial, or extrapericardial implantation are described in Heil, Jr. et al., U.S. Pat. No. 5,016,808, Fogarty et al., U.S. Pat. No. 4,860,769, and Hauser et al., U.S. Pat. No. 5,052,407. The electrodes of these patents use various construction techniques, including electrodeposition or vapor deposition onto a plastic tube, helically wound wire (round or ribbon, unifilar or multifilar, single or double helix) or conductive rings on a flexible insulating portion, and conductive screen wrapped around a tubular body.

Other defibrillation leads are disclosed in Mehra et al., U.S. Pat. No. 5,144,960, and in Bardy et al., U.S. Pat. No. 5,174,288.

Endotak SQ Model 0048 (Cardiac Pacemakers Inc., St. Paul, Minn., USA), described in "A Subcutaneous Lead Array for Implantable Cardioverter Defibrillators" by Jordaens et al., published in *PACE*, Vol. 16, July 1993, Part I, is an electrode system consisting of three conductive elements that can be subcutaneously inserted. The conductive elements of this "array lead" are made of electrically common multifilar coil, joined in a silicone yoke, and separately introduced with a lead tunneler and peel-away sheaths.

As defibrillator technology improves and the demand for defibrillators increases, it becomes increasingly desirable to have leads available that are easily implanted. Any implantable defibrillation electrode must be capable of withstanding repeated flexing over a long period of time. In addition, the electrode must have sufficient surface area to discharge high amounts of energy for effective defibrillation, and must maintain its electrical integrity. The electrode must be of biocompatible materials, as well as of a shape that avoids tissue damage.

SUMMARY OF THE INVENTION

The present invention provides a lead with an improved electrode design for use with an implantable defibrillator system. In the preferred embodiment, a transvenous electrode is constructed from six tiny platinum iridium space wound coils, space wound onto a silicone rubber tube, molded over with silicone rubber, then partially exposed by abrading away the molded silicone by grit blasting with sodium bicarbonate. This electrode exhibits a high degree of flexibility and therefore can be positioned quickly and easily within the right ventricle, right atrium, or superior vena cava, for example. Its flexibility also permits insertion of a curved stylet to aid in placement. Because of its flexibility, it can adapt to the complex movement of the heart, and will not perforate the endocardium. Because of its coiled coil structure, the wire within the electrode flexes very little with electrode movement; therefore, the fatigue life is high. The use of small coiled coils may provide an electrode having a resistance greater than about one ohm. While prior art systems attempt to minimize electrode resistance, this feature is used to advantage with the present invention wherein current flow from the electrode may be controlled or modified by changing the location where the lead conductor is electrically connected to the electrode.

In an alternative embodiment, this electrode construction can be used on a lead designed for epicardial placement.

In a third embodiment, an electrode of this construction can be used on a lead designed for subcutaneous placement.

It is thus an object of the present invention to provide a lead with an improved electrode for an implantable defibrillator.

It is a further object of the invention to provide a lead requiring less time for implantation.

It is an additional object of the invention to provide a lead with an electrode that is more flexible and fatigue resistant than existing electrodes.

It is another object of the invention to provide a lead with an electrode that is easily manufactured.

it is another object of the invention to provide a method of electrode construction that could be used to enhance the performance of the lead configurations of the prior art.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 7 shows a detail view of the electrical connection of the lead of FIG. 5;

FIG. 8 shows a cross sectional view of the proximal end of the electrode of FIG. 5;

DETAILED DESCRIPTION OF THE INVENTION

Figure 1:
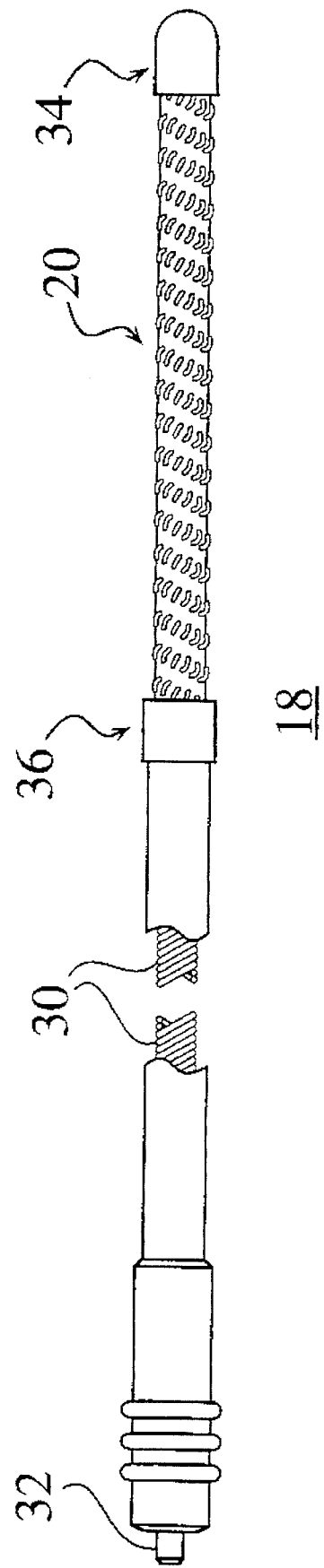
FIG. 1 illustrates the defibrillation electrode of novel construction of the present invention.

FIG. 1 shows a lead 18 having an electrode 20 electrically connected to a conductor coil 30 in two locations. The first connection 34 is at the distal end of electrode 20, and the second connection 36 is at the proximal end. These connections can be welds, crimps, and the like, in any combination. The conductor coil 30 is in turn electrically connected to connector 32 for coupling with a pulse generator such as the type described in U.S. Pat. No. 5,007,422 to Pless et al., which is assigned to the assignee of the present application. The lead body diameter is generally about 2.5 to 4.5 min.

Figure 2:
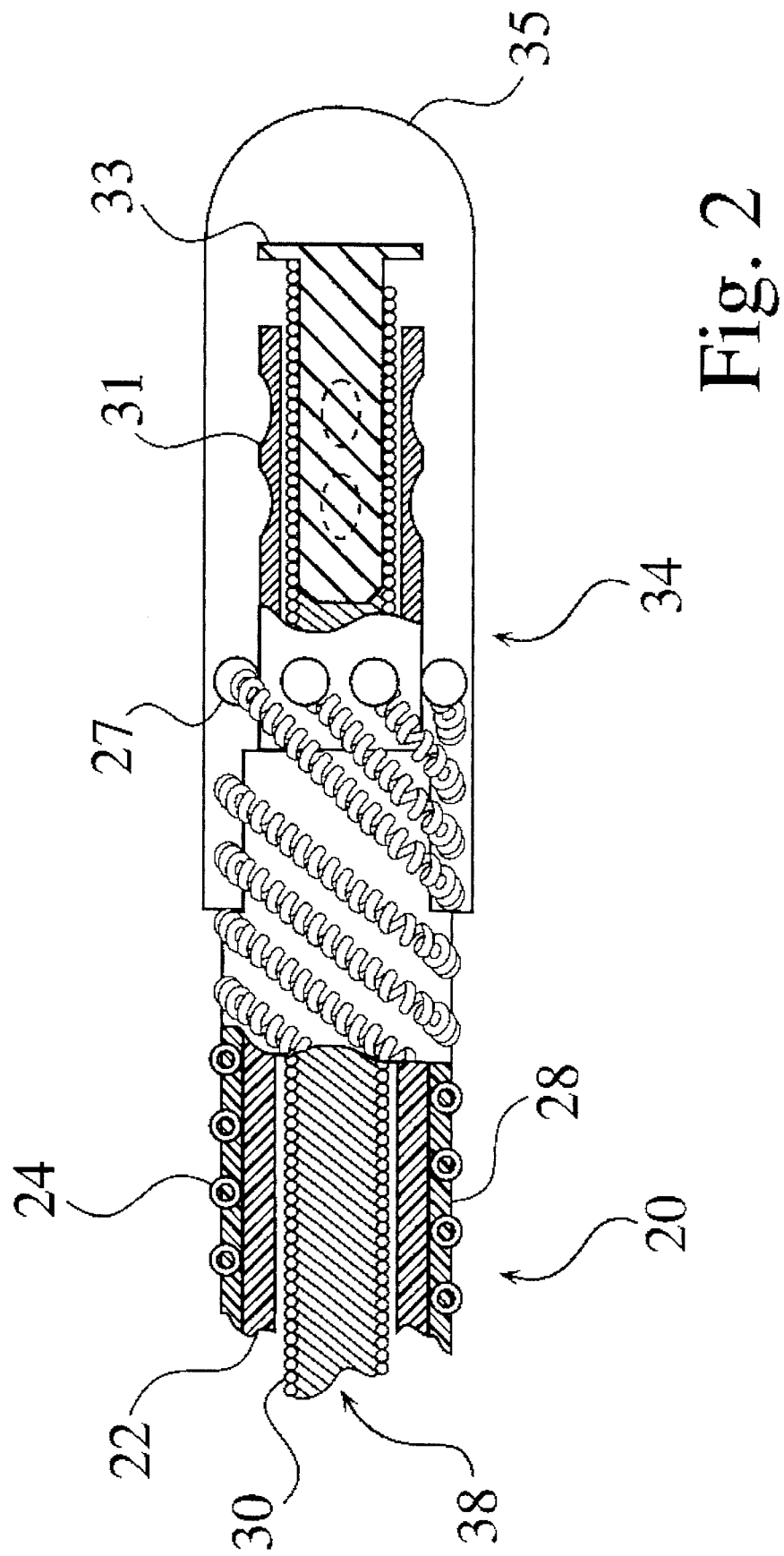
FIG. 2 is a detail view, partially cut away and partially in section, of the distal connection of the lead of FIG. 1.

FIG. 2 shows a detail view of the distal connection of the lead 18 of FIG. 1. Electrode 20 is shown to be constructed of many (six) electrode coils 24 helically wound around a flexible tubular supporting core 22, which may be either electrically conductive or insulative, and may be extruded or molded. This structure has elastomeric material 28, which also may be conductive or insulative, partially encapsulating the electrode coils. The many electrode coils increase conductivity and redundancy. One method of achieving this structure is to completely encapsulate the wrapped electrode coils, then abrade away the surface to partially expose the coils using the method of Mar et al., U.S. Pat. No. 5,226,260, which is assigned to the assignee of the present application and which is incorporated herein by reference. A conductor 30 extends through the lumen of core 22, making connection 34 at the distal end of electrode 20. Conductor 30 is crimped to a sleeve 31 and to a pin 33. The distal ends of electrode coils 24 are melted into balls 27, which are then welded to sleeve 31, forming an electrical connection to the conductor coil. This connection is also described in U.S. Pat. No. 5,488,768 to Mar, for a "Method of Forming a Defibrillation Electrode Connection" which is assigned to the assignee of the present application. The connection 34 is then covered by a protective cap 35, which may be electrically conductive or insulative. Protective cap 35 seals the electrode connection from body fluids. Conductor coil 30 forms an inner lumen 38 through which a stylet may be placed to stiffen the lead during implantation. Pin 33 serves both as a support for coil 30 and sleeve 31 for crimping, and as a stop for the stylet.

Figure 3:
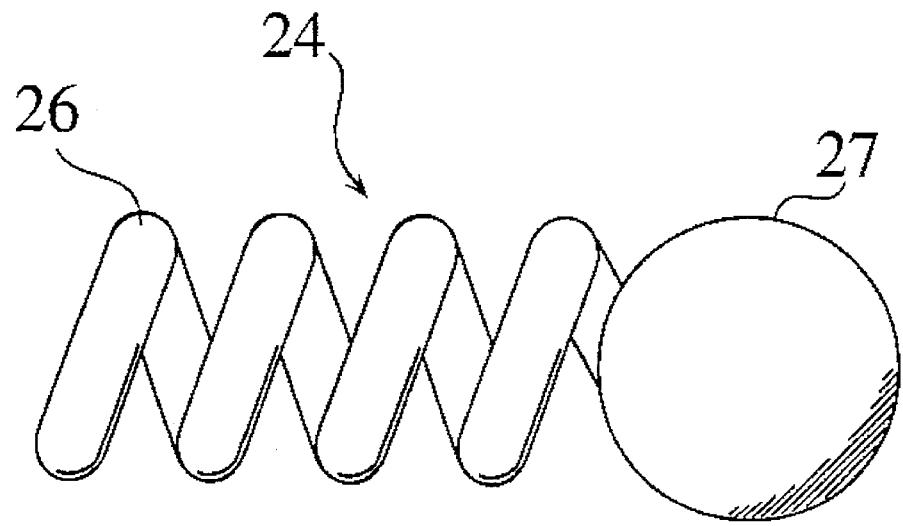
FIG. 3 is a detail view of the distal end of the electrode coil of FIG. 1.

FIG. 3 shows that each electrode coil 24 is made from a helically wound metal wire 26, which may be round or flat in cross section. This wire must be very strong, fatigue resistant, conductive, corrosion resistant, and biocompatible. Platinum iridium is one example of such a material. Electrode coil 24 is shown without an inner core; however, a thin wire or plastic filament could be located within coil 24 to provide either increased electrical conductivity, mechanical redundancy, or both. The filament could be metal or nylon, for example. In order for the lead to be sufficiently thin to be transvenously implantable, electrode coils 24 should be between about 0.2 and 0.4 mm, and wire 26 should be about 0.05 to 0.10 mm in diameter. Close winding of wire 26 into electrode coils 24 provides more exposed metal for charge transfer to tissue. However, space winding decreases the lengths of wire in the coils, decreasing end to end electrode resistance. Additionally, space winding provides more surface for matrix material to mechanically stabilize coils and allows for a substantial volume of matrix material that can flex with the heart and body motion instead of pulling away from the coils. Therefore, a certain amount of space is preferred, typically one-half to one wire diameter space between wires. Similarly, electrode coils 24 can be close or space wound onto core 22. The same general principles apply. The distal end of each electrode coil 24 is melted into a ball 27, which provides more volume of material to form a strong and reliable crimp or weld. This melted ball structure works particularly well when made of a noble material such as a platinum iridium alloy. A hydrogen torch, also called a "water welder", is one suitable means for melting the coil to form the ball. This device dissociates water into hydrogen and oxygen, then burns the hydrogen to form water again. This process burns cleanly, without incorporating byproducts into the melting coil, which is important for maintaining biocompatibility and material consistency for any subsequent welding.

Figure 4A:
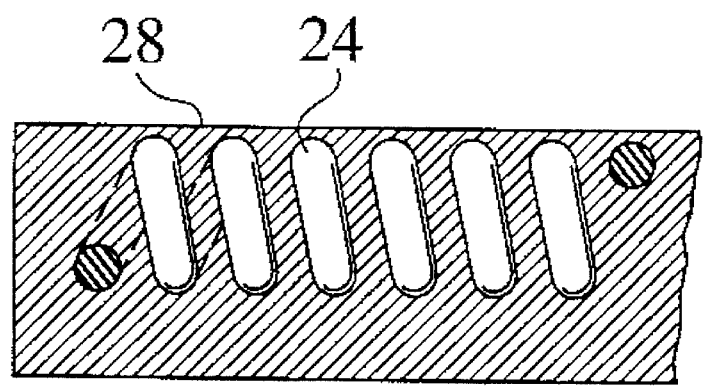
FIGS. 4A and 4B illustrate the electrode of FIG. 1 during two manufacturing steps.
Figure 4B:
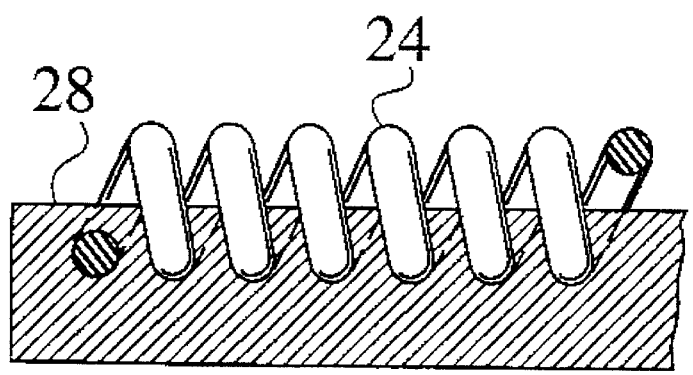

FIGS. 4A and 4B illustrate the process by which electrode coils 24 are embedded in elastomeric material 28, preferably silicone rubber. FIG. 4A shows electrode coil 24 as molded over by elastomeric material 28. FIG. 4B shows the structure of FIG. 4A, after a portion of elastomeric material 28 has been abraded away to partially expose electrode coil 24. The level of material removal is controllable. The more metal exposed, the greater the electrode surface area for defibrillation, but the less material for providing mechanical stability.

Figure 5:
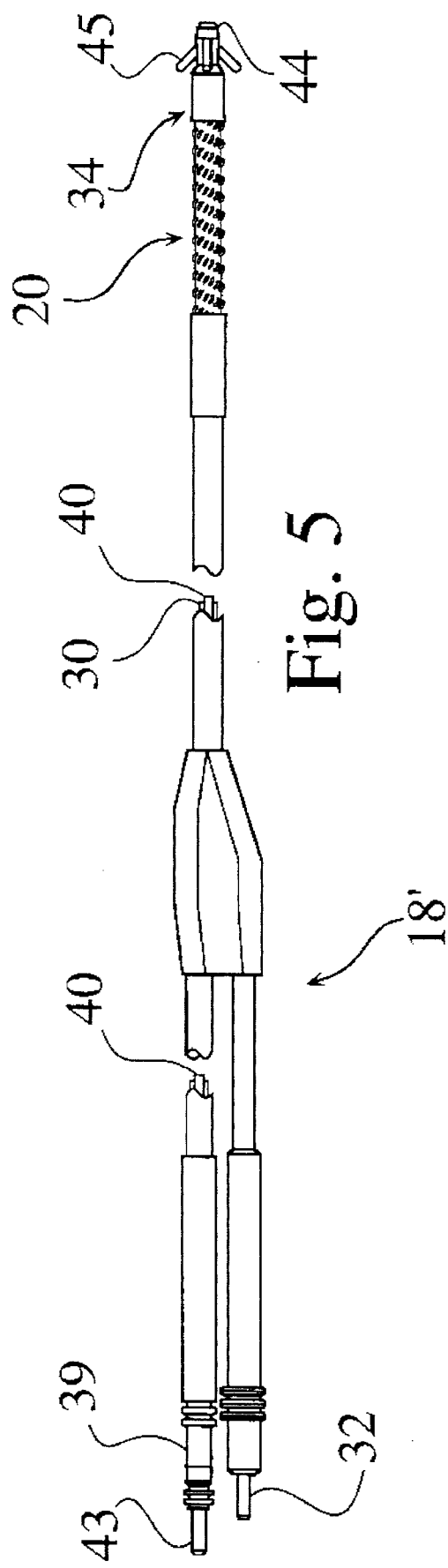
FIG. 5 illustrates an alternative embodiment of the invention which includes a pacing electrode, and uses the novel electrode for both defibrillation and sensing.

FIG. 5 shows a lead 18' with a pacing electrode 44, and electrode 20 which is used alternately for defibrillation and for sensing. Pacing electrode 44 may be of any of the numerous constructions known in the art. A fixation mechanism 45 is shown as tines, but may be any known in the art, including a screw used for both pacing and fixation. Pacing electrode 44 is electrically connected to a pacing conductor coil 40, which is in turn connected to a pacing connector 43. Electrode 20 is electrically connected at connection 34 to conductor coil 30, which is electrically connected to both defibrillation connector 32 and a sensing connector ring 39.

Figure 6:
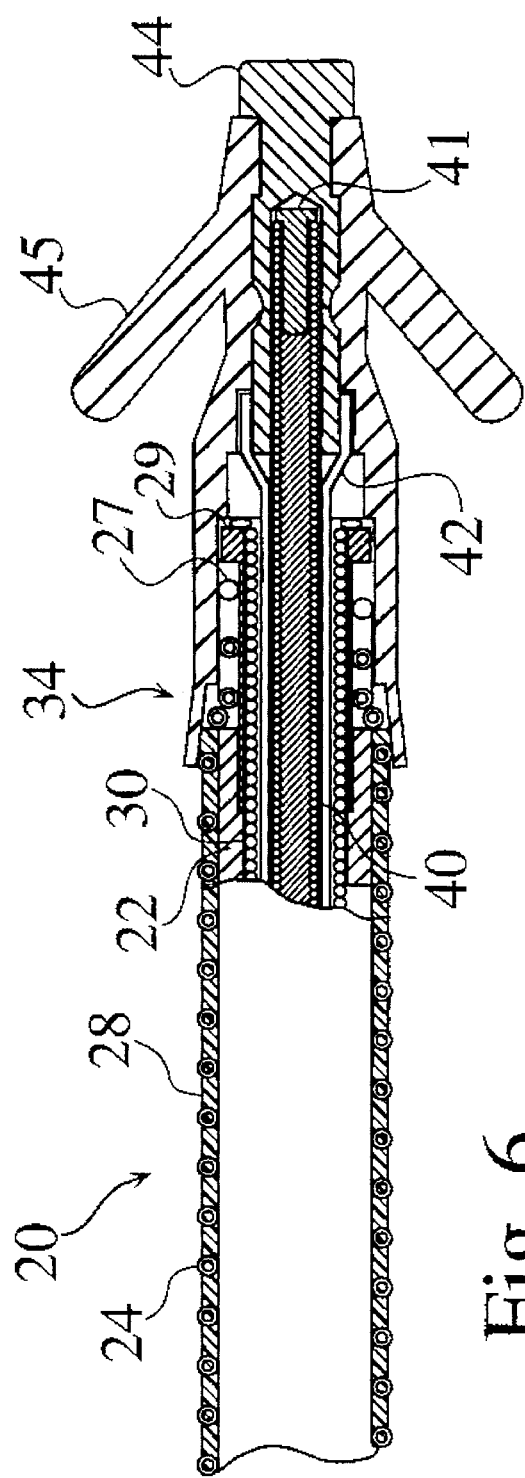
FIG. 6 shows a sectional view of the distal end of the lead of FIG. 5.

FIG. 6 shows a detail view of the distal end of the lead of FIG. 5. Electrode 20 is shown to be constructed of a plurality of electrode coils 24 helically wound around flexible tubular supporting core 22. This structure has elastomeric material 28 partially encapsulating the electrode coils. Conductor 30 extends through the lumen of core 22, making connection 34 at the distal end of electrode 20. Conductor 30 is welded to the face of sleeve 29, as described in U.S. patent application Ser. No. 08/018,832, filed Feb. 18, 1993 by Bush et al., for an "Electrical Connection for Medical Electrical Stimulation Electrodes" which is assigned to the assignee of the present application and which is incorporated herein by reference. The distal ends of electrode coils 24 are melted into balls 27, and are then welded to sleeve 29, forming electrical connection 34 to the conductor coil. A pacing conductor coil 40 extends through the lumen of tubular core 22 and is electrically insulated from conductor coil 30 by an insulator 42. Pacing conductor coil 40 is shown connected by a crimp connection to pacing electrode 44 and a crimp pin 41; this connection may alternatively be a weld.

FIG. 7 shows a detail view of electrical connection 34. The distal end of conductor coil 30 has been welded to the face of sleeve 29. Electrode coils 24 have had their distal ends melted into balls 27, then welded to the outside surface of sleeve 29.

FIG. 8 shows a cross sectional view of the proximal end of electrode 20. Two groups of electrode coils 24 have their proximal ends melted into balls 27' to provide electrical redundancy. Molded electrode core tube 22 has two pockets 25 in its proximal end into which balls 27' are placed prior to wrapping electrode coils 24 onto tube 22. After elastomeric material 28 is applied, an electrical insulation 37 is joined to electrode 20 using a joining material 47, for example silicone rubber. A mandrel is used to keep the lumen open during this process, so that the conductor can be passed through the joint and connected at the distal end of electrode 20.

Figure 9:
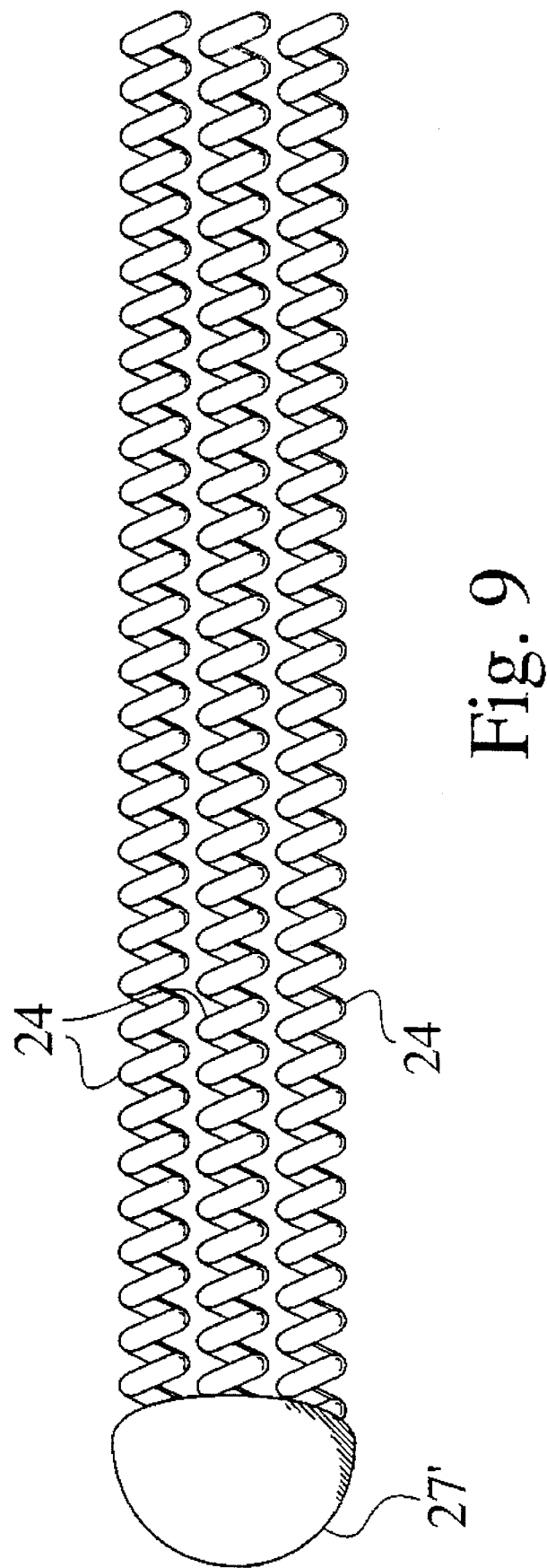
FIG. 9 illustrates one step in the manufacture of the lead of FIG. 5.

FIG. 9 shows one group of three electrode coils 24 with proximal ends melted into ball 27'. This group of three electrode coils can be wound onto a tube such as core tube 22 of FIG. 8 in several ways. The preferred method is to insert a mandrel into a molded core tube, place the mandrel into a lathe-type coil winder, insert one group of three electrode coils 24 into each of two pockets of the tube, then use the coil winder to wind the electrode coils 24 around the tube. After the electrode coils 24 are wound onto the core tube, elastomeric material may be compression molded over the coils and core. An alternative method is to embed electrode coils 24 into uncured elastomeric material that has been rolled into thin strips, then wrap the coil embedded strips of elastomeric material around a core tube, then cure the elastomeric material. A third alternative is to apply uncured elastomeric material to a cured core, then wind electrode coils 24 about the core, embedding them into the elastomeric material. Yet a fourth alternative is to manufacture the core and elastomeric material portion simultaneously by putting uncured rubber onto a mandrel to form both portions; electrode coils 24 are then embedded into the surface of the rubber, and the rubber is cured.

Figure 10:
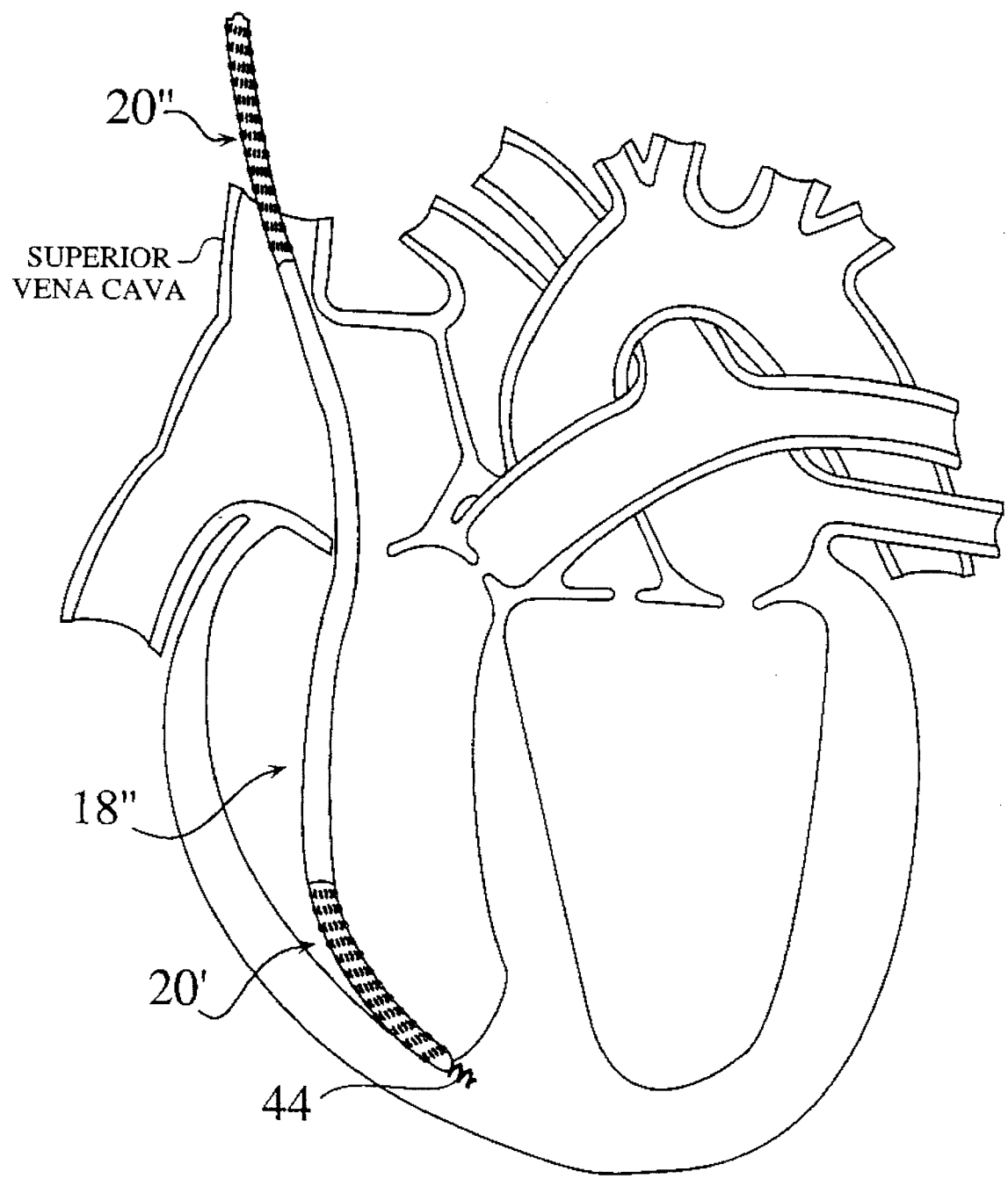
FIG. 10 is a lead implanted in the heart that includes two defibrillation electrodes and a pacing electrode.

FIG. 10 shows a lead 18" with two defibrillation electrodes, 20' and 20", having opposite polarity, and a pacing electrode 44 as it is positioned within a patient's heart. Electrode 20' acts alternately as a defibrillation electrode and as a sensing electrode. The lead is shown as situated in the heart, with pacing electrode 44 and distal defibrillation electrode 20' in the right ventricle, and proximal defibrillation electrode 20" located in the superior vena cava.

Figure 11:
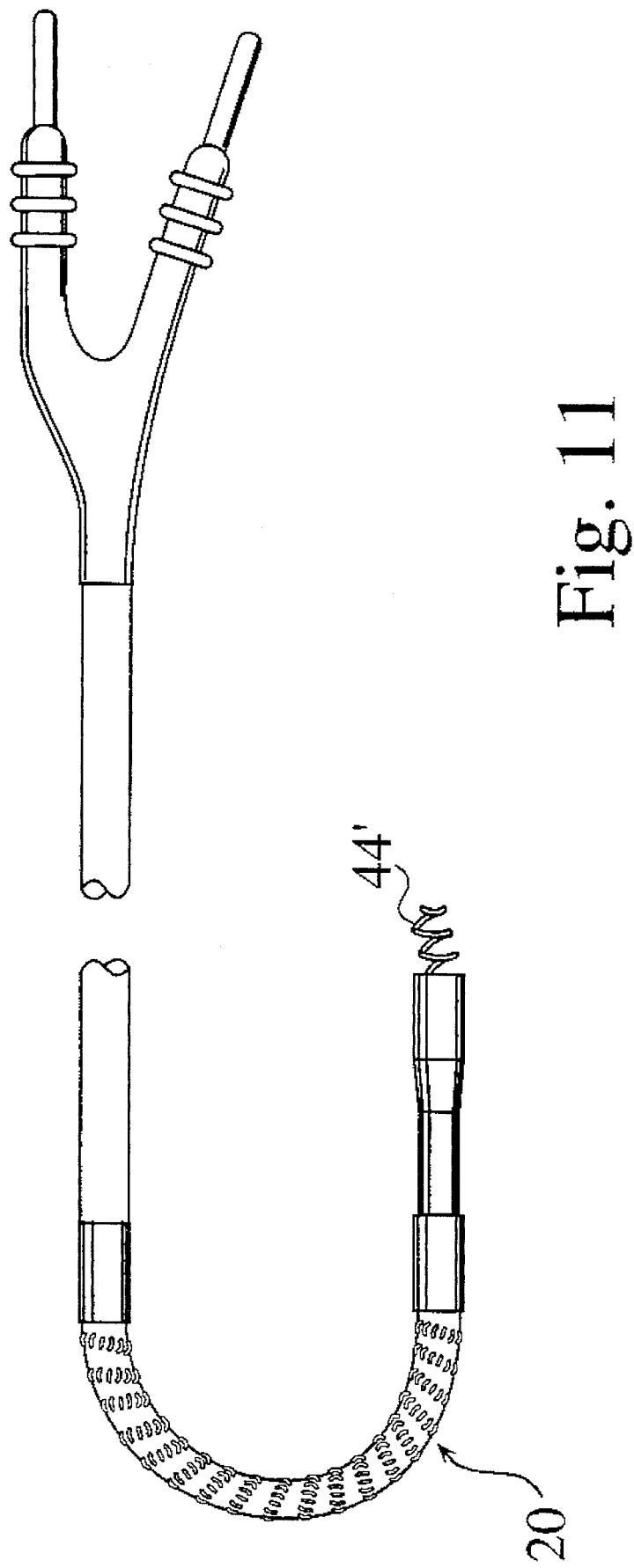
FIG. 11 shows a J-shaped lead.

FIG. 11 shows a lead with a J shaped defibrillation electrode 20 and with screw in tip 44', for use in the right ventricle or atrium, for example. Screw in tip 44' can be used for pacing and fixation, or for fixation alone. The preferred method of manufacturing a J shaped lead is to start with a tubular core which has been molded in a J shape. The J shaped tubular core is then straightened by inserting a mandrel into it. Then, electrode coils as described above are wound onto the straightened core. The tubular core and electrode coils are then reformed into the J shape by removing the straight mandrel, perhaps replacing it with a J shaped one. The tubular core with electrode coils is then molded over with elastomeric material, holding the electrode coils in their final J shape.

Figure 12:
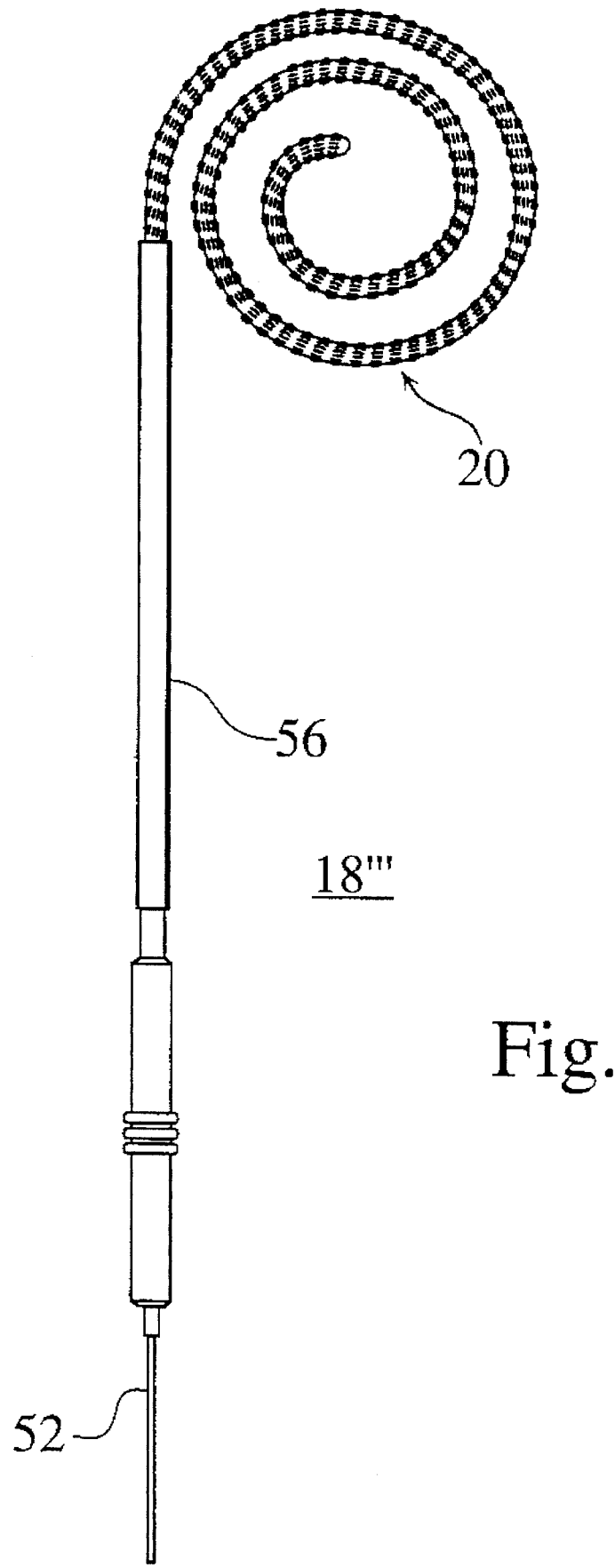
FIG. 12 shows a spiral-shaped lead and means to deploy it.

FIG. 12 shows a spiral electrode 20, and means for deploying it. A stylet 52 is inserted through lead 18''' and is used to push electrode 20 through an introducer sheath 56.

Figure 13:
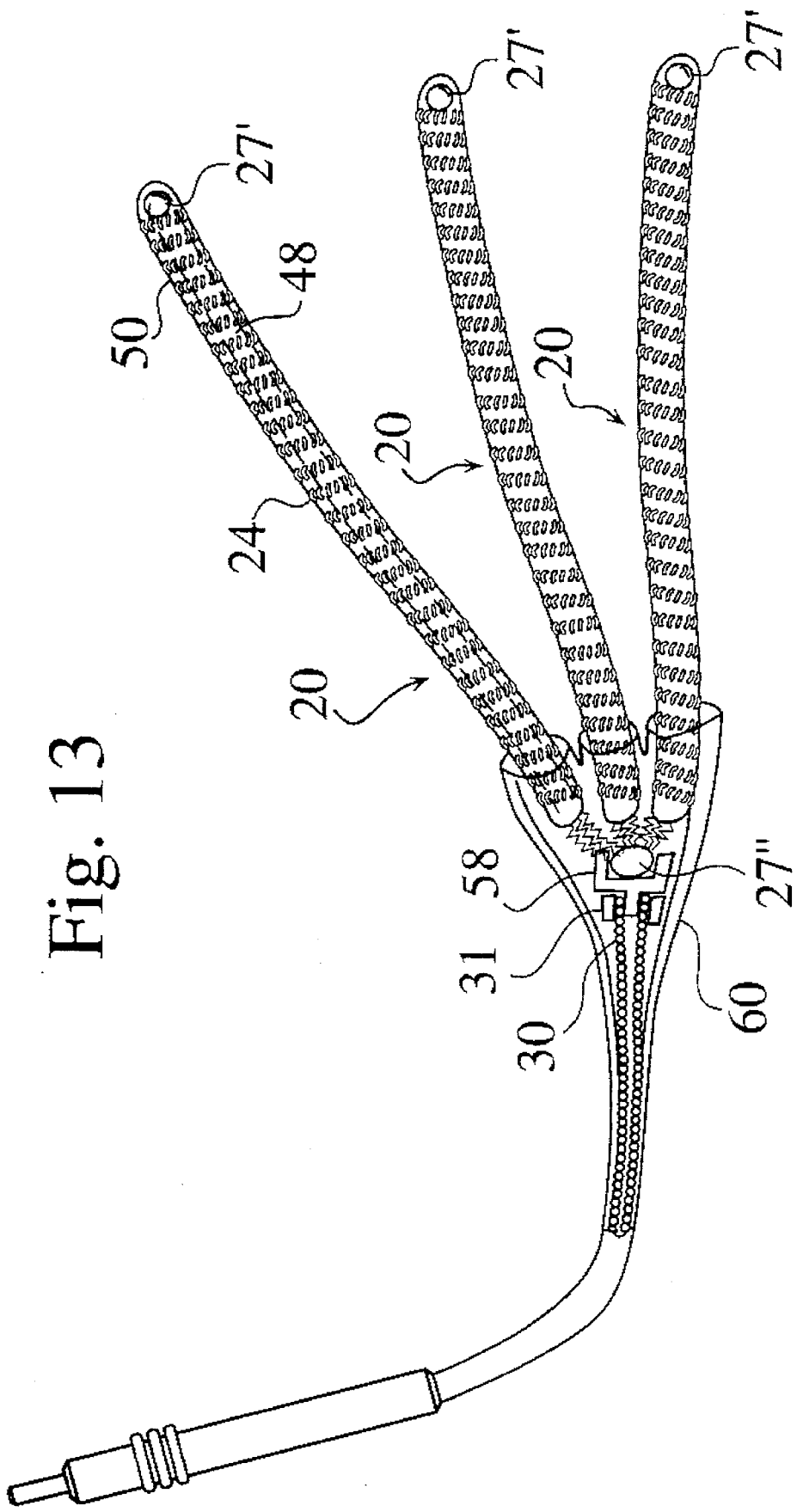
FIG. 13 shows a detail view of an electrode connection of a lead with several electrodes in parallel for subcutaneous implantation.

FIG. 13 illustrates a lead with three electrodes 20, intended for implantation subcutaneously on the left lateral part of the chest. They are of the same polarity, and are connected to a common node on conductor 30. Electrode coils 24 are connected at distal ends by melted balls 27' and wound onto flexible cores 48. Flexible embedding material 50 partially covers electrode coils 24. The proximal ends of electrode coils 24 are all connected by melting them into ball 27". Ball 27" is crimped into metal joining piece 58. Also crimped to metal joining piece 58 is crimp sleeve 31 and conductor coil 30. A protective strain relief molding 60 encapsulates the entire connection.

Because the electrode coil wire is longer and thinner than the electrode elements of the prior art, the electrode of the present invention can be made with a certain amount of resistance along its length, say, 3 to 15 ohms. This property of the electrode can be used to direct defibrillation energy to selected regions of the heart by careful choice of connection locations of electrode to conductor. For example, if the electrode 20 of FIG. 5 were placed with its distal end in the apex of the RV, current would be steered to the RV apex since that is where the conductor attaches to the electrode at connection 34. On the other hand, because of the electrode connections 34 and 36 on either end of electrode 20 of FIG. 1, the current distribution would be more even along the electrode length than in the electrode of FIG. 5, since the potential is the same at either end, assuming a very low resistance conductor 30. In this case, the end to end electrode resistance is also reduced, with the highest resistance being in the middle of the electrode. The connection could also be made in the middle of the electrode, instead of or in addition to the ends. With the electrode connected to the conductor in only the middle of the electrode and not the ends, current density would be more even since end effects would be reduced. Several connections between the conductor and the electrode may be made along the length of one electrode. This is desirable for reducing overall resistance, particularly when the electrode is long, as in the lead of FIG. 12.

The above has been offered for illustrative purposes only and is not intended to limit the scope of the invention of this application, which is as defined in the claims below.

That which is claimed is:

1. A method of manufacturing a body implantable lead for use with a pulse generator, comprising the steps of:

providing a tubular core;

helically winding at least one wire to form at least one electrode coil;

winding said at least one electrode coil about said tubular core; and applying an elastomeric matrix material onto said tubular core and said electrode coils.

2. The method of claim 1 and further comprising the step of placing said tubular core on a mandrel prior to winding said at least one electrode coil about said tubular core.

3. The method of claim 1 and further comprising the step of removing a portion of said elastomeric matrix material to partially expose said at least one electrode coil.

4. The method of claim 3 in which removal of said portion of matrix material is accomplished by abrasion.

5. The method of claim 1 in which said tubular core is molded.

6. The method of claim 1 in which said tubular core is extruded.

7. The method of claim 1 wherein said step of providing a tubular core comprises molding a tubular core tube having at least one pocket.

8. The method of claim 7 wherein each of said electrode coils has a proximal end, and further including the step of placing said proximal end into a corresponding one of said pockets.

9. The method of claim 1 wherein said steps of providing a tubular core comprises providing an electrically conductive tubular core.

10. The method of claim 1 wherein said step of providing a tubular core comprises providing an electrically insulative tubular core.

11. The method of claim 1 wherein said step of helically winding at least one wire to form at least one electrode coil comprises close winding said at least one wire to form said at least one electrode coil.

12. The method of claim 1 wherein said step of helically winding at least one wire to form at least one electrode coil comprises space winding said at least one wire to form said at least one electrode coil.

13. The method of claim 1 and further including the step of locating a wire filament within said electrode coil.

14. The method of claim 1 and further including the step of locating a plastic filament within said electrode coil.

15. The method of claim 1 wherein said steps of winding said at least one electrode coil about said tubular core and of applying an elastomeric matrix material onto said tubular core and said electrode coils comprises rolling uncured elastomeric matrix material into strips, embedding said electrode coils into said uncured elastomeric matrix material, wrapping said strips of elastomeric matrix material around said tubular core, then curing said elastomeric matrix material.

16. The method of claim 1 wherein said step of applying an elastomeric matrix material onto said tubular core and said electrode coils comprises applying a conductive elastomeric matrix material onto said tubular core and said electrode coils.

17. The method of claim 1 wherein said step of applying an elastomeric matrix material onto said tubular core and said electrode coils comprises applying an insulative elastomeric matrix material onto said tubular core and said electrode coils.

18. A method of manufacturing a body implantable lead for use with a pulse generator, comprising the steps of:

providing a J shaped tubular core;

helically winding at least one wire to form at least one electrode coil;

straightening said J shaped tubular core on a mandrel;

winding said at least one electrode coil about the straightened J core;

reforming said tubular core and electrode coils into a J shape; and molding an elastomeric matrix material onto said tubular core and said at least one electrode coil.

19. The method of claim 18 and further comprising the step of removing a portion of said elastomeric matrix to expose a portion of said at least one electrode coil.

20. The method of claim 18 wherein said step of providing a J shaped tubular core comprises molding a J shaped tubular core.

21. The method of claim 18 wherein said step of reforming said tubular core and electrode coils into a J shape comprises replacing said straight mandrel with a J shaped mandrel.

22. A method for manufacturing a body implantable lead for use with a pulse generator, comprising the steps of:

putting uncured rubber onto a mandrel;

helically winding at least one wire to form at least one electrode coil;

embedding said electrode coils into said rubber; and curing said rubber.

\* \* \* \* \*